(12) United States Patent
Bason

(10) Patent No.: US 6,283,365 B1
(45) Date of Patent: Sep. 4, 2001

(54) INDICATOR DEVICE

(76) Inventor: Neil Peter Bason, 52a Berkshire Drive, Congleton, Cheshire, CW12 1SB (GB)

( * ) Notice: Subject to any disclaimer, the term of this patent is extended or adjusted under 35 U.S.C. 154(b) by 0 days.

(21) Appl. No.: 09/288,163

(22) Filed: Apr. 8, 1999

(30) Foreign Application Priority Data

Apr. 9, 1998 (GB) .................................................. 9807558

(51) Int. Cl.[7] .............................................. G06C 27/00
(52) U.S. Cl. ........................................... 235/116; 235/117
(58) Field of Search .................................. 235/117, 116; 604/207

(56) References Cited

U.S. PATENT DOCUMENTS

| | | | | |
|---|---|---|---|---|
| 3,792,242 | * | 2/1974 | Hanson ................................ | 235/117 |
| 4,599,508 | * | 7/1986 | Smetaniuk ........................... | 235/116 |
| 5,482,030 | * | 1/1996 | Klein ................................... | 128/200 |
| 5,505,192 | * | 4/1996 | Samiotes et al. ................... | 128/200.14 |
| 5,622,163 | * | 4/1997 | Jewett et al. ...................... | 128/200.23 |
| 5,957,896 | * | 8/1997 | Bendek et al. ...................... | 604/207 |

\* cited by examiner

*Primary Examiner*—Karl D. Frech
(74) *Attorney, Agent, or Firm*—Samuels, Gauthier & Stevens

(57) ABSTRACT

A dose counter attached or attachable to the base of a pressurised canister for a metered dose inhaler and comprising a spring-loaded cap (14) which may be depressed in relation to a second part (1) mounted on the domed base of the canister (C). Within the cap (14) is a pair of independently rotatable rings, each carrying on its upper surface indicia visible through a window (13) in the cap. For each depression of the cap (14) relative to the canister, the first ring (4) is indexed in rotation, and for each complete revolution of the first ring (4), the second ring (8) is indexed in rotation. The first ring (4) carries the numbers 0 to 9 and the second ring (8) carries the numbers 00 to 20 so that the device counts down progressively from 200 to 000 thus providing an incremental indication of the number of doses remaining in the canister.

8 Claims, 5 Drawing Sheets

INDICATOR DEVICE

THIS INVENTION concerns an indicator device, and particularly, though not exclusively, such a device adapted to serve as a dose counter for metered dose inhalers (MDI's).

MDI's include pressurised canisters containing drugs to be inhaled for the relief of, for example, the symptoms of asthma. Typically each canister contains 200 doses but conventionally provides no indication to the user as to how many doses remain available for use at a particular time. This results in considerable inconvenience and risk to the user who must, inevitably, carry a fresh replacement MDI in addition to the one currently in use thus to ensure that if the current one becomes empty there is a spare supply.

Thus there is a need for a dose counter for an MDI to indicate the number of times the pressurised canister is depressed to dispense a dose of the drug. Such a counter must count down, typically from 200 to zero, progressively as doses are administered so that the user can readily see how many doses remain.

According to the present invention there is provided an indicator device to provide a count of a series of like linear movements of a first part of the device with respect to a second part thereof; the first part comprising first and second rotational rings carrying indicia progressively visible on the first part; the first and second parts having inter-engaging spaced projections such that upon each linear movement of the first part the first rotational ring is indexed in rotation, and such that a upon a predetermined number of linear movements of the first part, the second rotational ring is indexed in rotation.

Preferably, the second part is adapted to be affixed to the base of a pressurised canister of an MDI, and the first part is captive on the second part and spring-loaded thus to be capable of depression relative to the second part and to the canister.

Still further, the rotational rings are concentrically arranged, and the first rotational ring includes an annular array of spaced projections engageable successively with two further annular sets of projections fixed with respect to the second part of the device such that the projections on the first rotational ring successively engage the fixed projections to cause the first rotational ring to index in rotation twice for each depression and release thereof.

Furthermore, the second rotational ring comprises a further set of projections engageable successively by a pawl attached to the first rotational ring upon each complete revolution thereof thus to index the second rotational ring by one increment for each revolution of the first ring.

Still further, the first part of the device comprises a cap adapted for linear movement but prevented from rotational movement in relation to the second part of the device, the cap including a profiled channel in which the pawl is adapted to travel during rotation of the first rotational ring, the profile of said channel causing the pawl to engage the projections of the second rotational ring once for each revolution of the first rotational ring, the cap including a window through which respective surfaces of the first and second rotational rings are visible in one radial location thereof whereby numeric indicia on said surfaces are progressively visible through said window.

An embodiment of the invention will now be described, by way of example only, with reference to the accompany drawings, in which.

Figure 1:
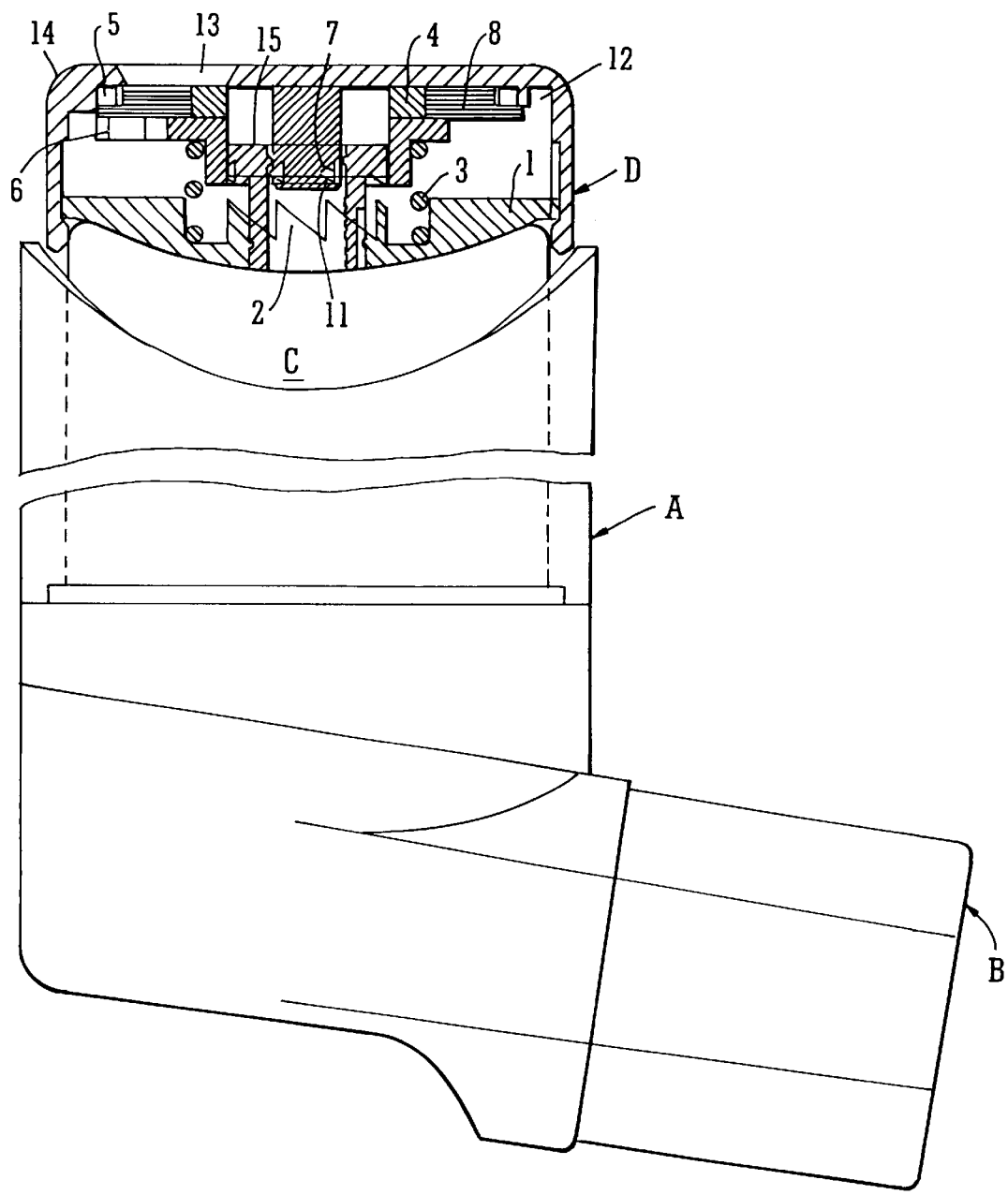
FIG. 1 is a part cross-sectional view of a meter dose inhaler having thereon an indicator device in accordance with the invention.
Figure 2:
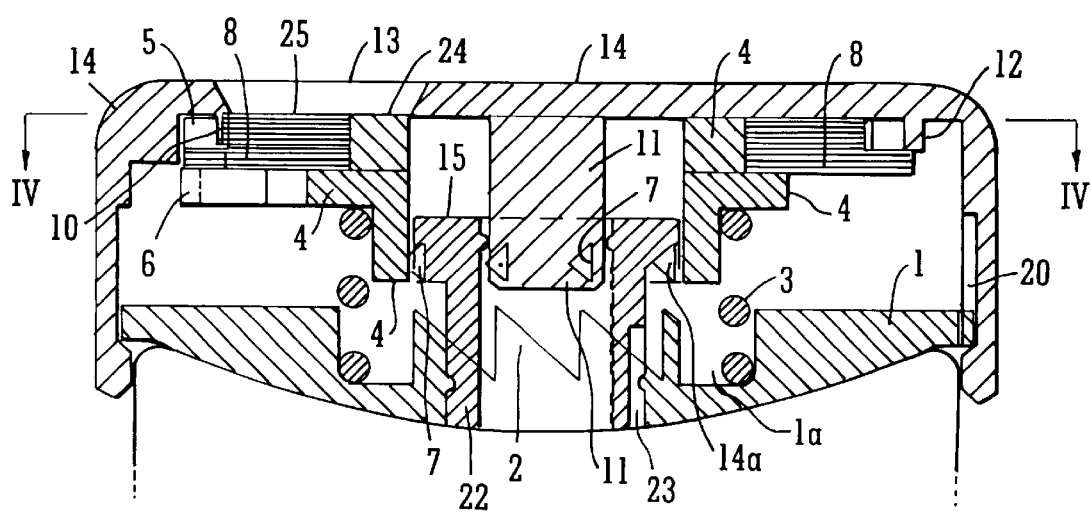
FIG. 2 is an enlarged cross-sectional view of the indicator device.
Figure 3:
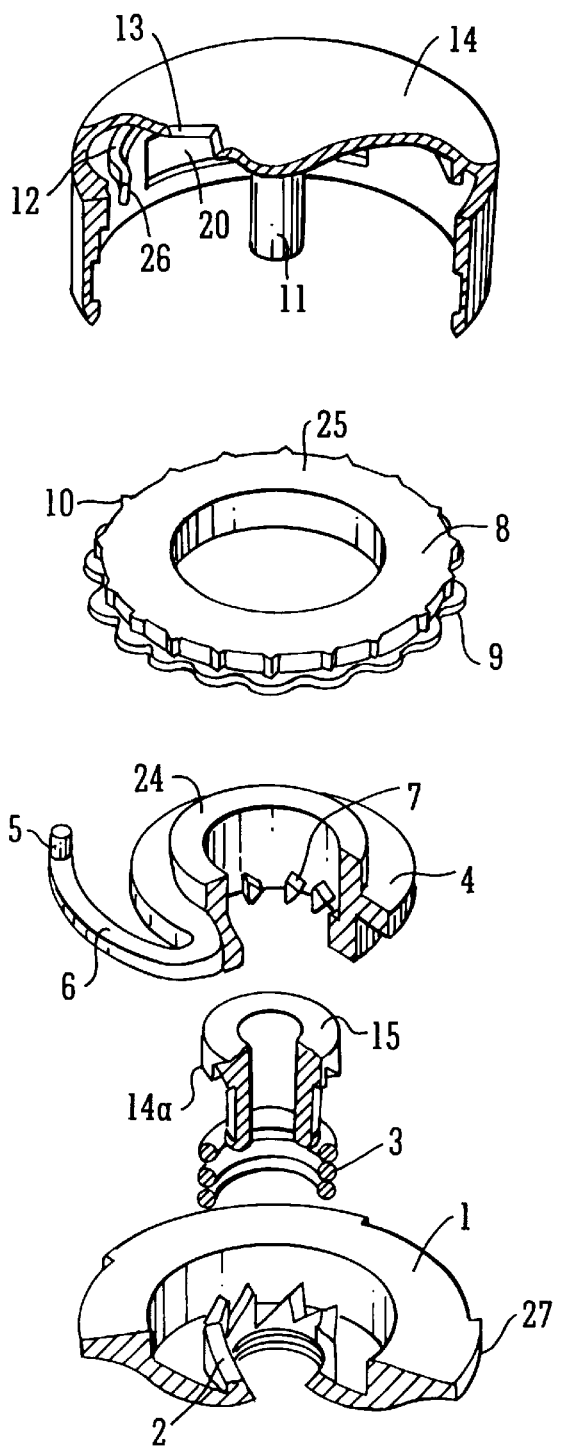
FIG. 3 is an exploded perspective view of the parts of the device.
Figure 4:
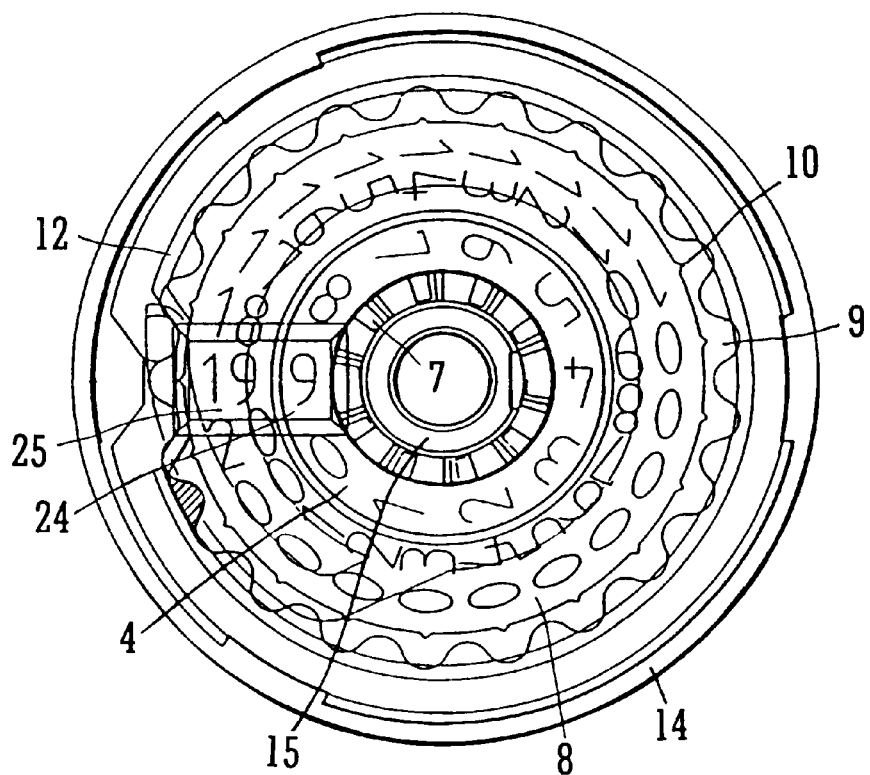
FIG. 4 is a plan view of the device taken on line IV—IV of FIG. 2.

Referring to FIGS. 1 to 3, a meter dose inhaler A includes a mouth-piece B through which a user may inhale a drug dispensed from a canister C removably contained within the inhaler. A counter in accordance with the invention is illustrated generally at D.

The counter consists of a first part or base 1 which, in manufacture of the canister C is bonded to the domed base thereof. If will be appreciated that the canister C and counter D comprise a replaceable item within the inhaler.

Disposed in fixed position on the base 1 is a central bush 15 which in assembly of the device has a part 22 located on the base 1 by of a key way 23 and is thus non-movably attached thereto. The base 1 defines an annular cavity 1a intended to house the bottom of a coil spring 3, the top of which engages beneath a radially outwardly directed flange of a first rotational ring 4, an inner annular part of which may be accommodated within the cavity 1a.

The ring 4 defines an inner cylindrical space within the lower end of which there is located an annular series of projections formed as inwardly directed triangular teeth 7.

At the inner extremity of the cavity 1a of base 1 there is an annular series of projections formed as upwardly directed teeth 2, and on the underside of an upper flange of the central bush 15 there is an annular series of projections formed as downwardly directed teeth 14a. When ring 4 is assembled with central bush 15, the triangular teeth 7 are movable therewith between the teeth 2 and the teeth 14a for a purpose to be described.

At one circumferential position on the outwardly directed flange of ring 4 is an outwardly projecting curved arm 6 carrying at its free end an upwardly directed pawl 5 for a purpose to be described.

Concentrically disposed above and around the ring 4 is a second rotational ring 8 having a circumferential series of projections formed as outwardly directed curvilinear teeth 9 and a further series of angular teeth 10 disposed on a reduced circumference of the ring 8. It will therefore be seen that the base 1, the central bush 15, the ring 4 and the ring 8 may be assembled in concentric relationship and surrounded by a cap 14 having a flat top and depending cylindrical wall, and having a central boss 11 which locates within the central bush 15. The cap 14 becomes captive with the base 1 by means thereon of an annular series of outwardly projecting lugs 27 which locate within arcuate and radially directed recesses 20 on the inner face of the cylindrical wall of the cap 14. The upper circular part of the cap 14 includes a window 13 of elongate rectangular form extending radially across one part of the top for a purpose to be described.

Within the cap 14 close to its circumference is a downwardly directed wall 12 defining an outer profiled channel which receives the pawl 5 of ring 4 when the device is fully assembled. The channel is profiled such that in one radial position which coincides with the position of window 13, the channel has a radially inwardly directed kink 26 (FIG. 3) for a purpose to be described.

When the entire device is assembled there is visible through the window 13 one radial location of the upper faces 24 and 25 respectively of the rotational rings 4 and 8. These faces carry respectively two numeric series such that face 24 carries the series 0 to 9 while face 25 carries the series 00 to 20. Thus, through the window 13 there may be visible progressively the numbers 000 to 200. As will be described the device counts down so that when the MDI is new and unused the number 200 will be visible thus indicating that there are 200 doses available within the canister to which the device is attached. As the MDI is progressively used the available doses will count down eventually to zero indicating that the canister is empty. The user may therefore determine at any time how many doses remain available from the canister.

The device operates as follows:

Upon depression of the cap 14 with respect to the base 1, the rings 4 and 8 are also depressed linearly causing, upon each depression, the teeth 7 to engage the lower fixed set of teeth 2. Owing to the triangular formation of the teeth 7 and 2 this causes the ring 4 to be indexed in rotation, (See FIG. 5) and upon return or release of the cap, the teeth 7 then engage the upper teeth 14a causing a further rotational movement of the ring 4. Each of these rotational movements represents one half of a complete movement of the ring 4 so that the number visible through the window 13 on face 24 will change by one point for a complete depression and release of the cap. Thus the user can see the progressive movement of the inner ring indicating a count down from 9 to 0 for a complete revolution of the ring 4. During such revolution the pawl 5 on arm 6 travels around the channel defined by the wall 12 in cap 14. After ten rotational movements of the ring 4 the pawl 5 engages the kink 26 in the channel and thus moves inwardly to engage an adjacent trough between two of the teeth 9 on the second rotational ring 8 causing the latter to move rotationally by one position before the pawl 5 leaves the kink 26 and returns to the main part of the channel. (See FIGS. 6a to 6d). Except when moved by the pawl, the ring 8 is prevented from rotational movement by engagement of one of the teeth 10 in a V-notch 30 in the inner face of the wall 12 coincident with the kink 26 therein (See FIG. 6a). Also, the ring 4 is prevented from rotation, except when being indexed, by engagement of the teeth 7 with the teeth 14a.

Thus it will be seen that for each complete revolution of the ring 4 the ring 8 is moved one position. When the device is new and unused the number 200 will appear in the window 13. The first actuation of the device moves rings 4 and 8 simultaneously thus revealing the number 199. Thereafter for ten operations the ring 4 alone will move to display a count down from 199 to 190 whereupon the outer ring 8 is moved once again to reveal the number 189 and so on, the device providing a continuously diminishing count of 200 doses from the MDI.

Figure 5:
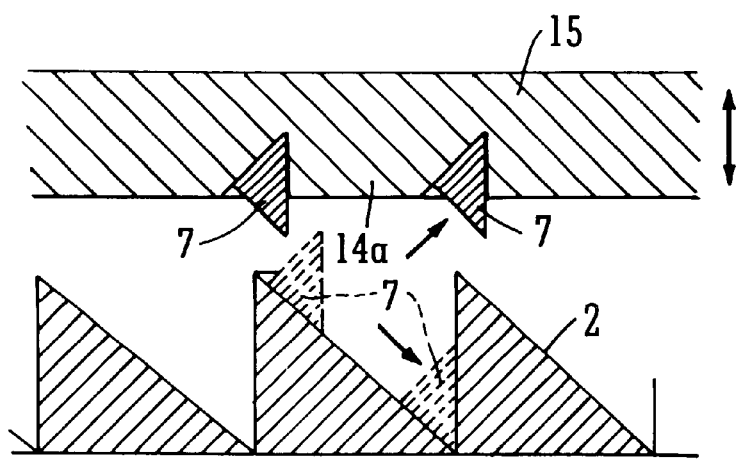
FIG. 5 is a cross-sectional view of part of the device illustrating the action thereof.
Figure 6A:
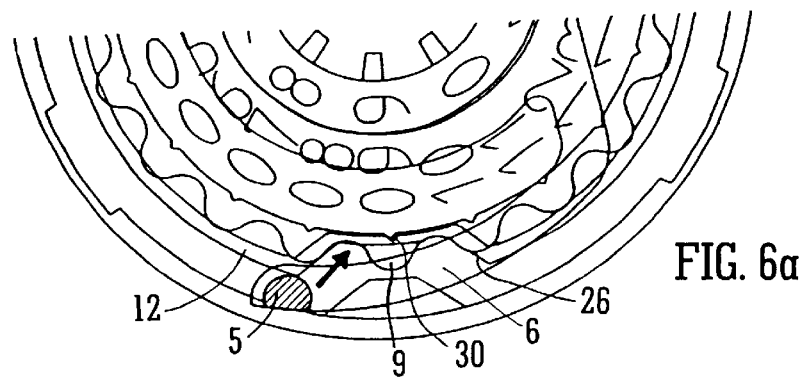
FIGS. 6a to 6d are partial plan views similar to FIG. 4, showing different operational conditions of the device.
Figure 6B:
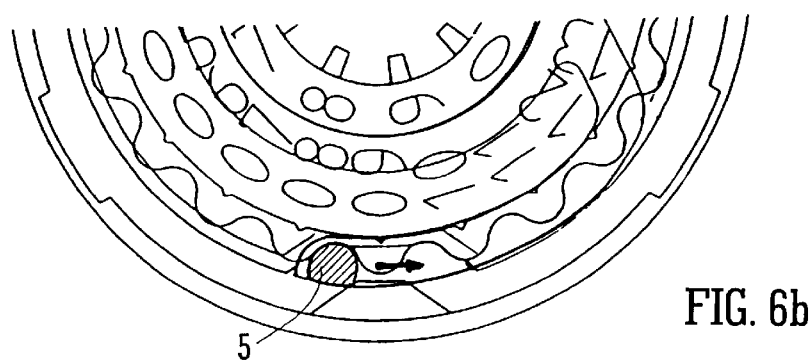
Figure 6C:
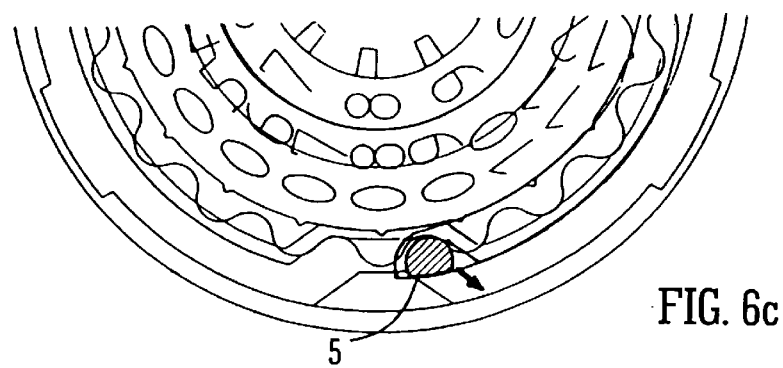
Figure 6D:
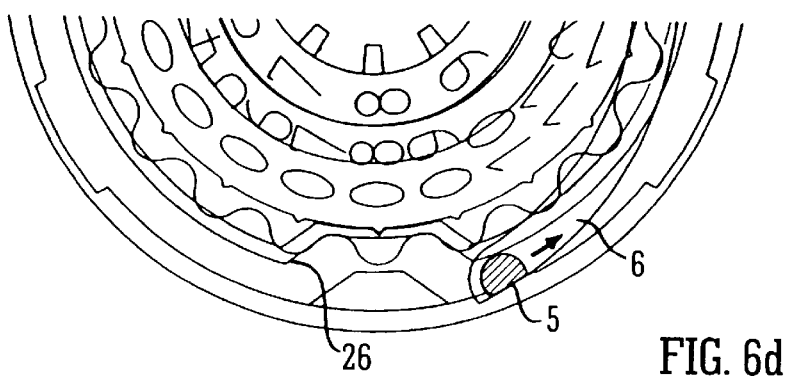

FIG. 5 serves to illustrate how depression and release movements of the device cause the teeth 7 to engage the teeth 2 and 14a progressively. FIGS. 6a to 6d illustrate how the pawl 5 enters the kink 26 and engages the teeth 9 of the ring 8 once for each complete revolution of the ring 4.

Preferably, the entire device with the possible exception of spring 3 is made from individual pieces moulded from a plastics material and assembly is initiated by passing the central bush 15 downwardly through the ring 4 and fixing it within the base 1, the ring 8 then being superimposed on the ring 4 and finally the cap 14 being introduced over the entire assembly with the central boss 11 located within the central bush 15.

Conceivably, the counter may be removably attached to the base of a canister thus to be re-usable, but from an economic point of view it is more likely that the counter will be permanently attached to a canister and thus supplied and disposed of along with it.

What is claimed is:

1. An indicator device to provide a count of a series of like linear movements of a first part of the indicator device with respect to a second part thereof; the first part comprising first and second concentric rotational rings carrying indicia progressively visible on the first part; the first and second parts having inter-engaging spaced projections such that upon linear movement of the first part the first rotational ring is indexed in rotation, and such that upon a pre-determined number of linear movements of the first part, the second rotational ring is indexed in rotation; wherein the first part is captive on the second part and spring-loaded thus to be capable of depression and release relative to the second part; and wherein the first rotational ring includes an annular array of said spaced projections engageable successively with two further annular sets of projections fixed with respect to the second part of the device such that the projections on the first rotational ring successively engage the fixed projections to cause the first rotational ring to index in rotation twice for each depression and release of the first part.

2. An indicator device according to claim 1, wherein the second part is adapted to be affixed to the base of a pressurised canister of a metered dose inhaler (MDI).

3. An indicator device according to claim 1, being adapted for removable attachment to a pressurised canister for a metered dose inhaler.

4. An indicator device according to claim 1, wherein the second rotational ring comprises a further set of projections engageable successively by a pawl attached to the first rotational ring upon each complete revolution thereof thus to index the second rotational ring by one increment for each revolution of the first ring.

5. An indicator device according to claim 4, wherein the first part of the device comprises a cap adapted for linear movement but prevented from rotational movement in relation to the second part of the device, the cap including a profiled channel in which the pawl is adapted to travel during rotation of the first rotational ring, the profile of said channel causing the pawl to engage the projections of the second rotational ring once for each revolution of the first rotational ring, the cap including a window through which respective surfaces of the first and second rotational rings are visible in one radial location thereof whereby numeric indicia on said surfaces are progressively visible through said window.

6. An indicator device according to claim 5, wherein the surface of the first ring carries a numeric series from 0 to 9, the surface of the second ring carries the numeric series 00 to 20, said surfaces being arranged concentrically such that through the window there may be visible progressively the numbers 000 to 200.

7. An indicator device according to claim 1, wherein the first and second rotational rings include means for preventing rotation thereof except when being indexed in rotation by the interengaging spaced projections.

8. An indicator device according to claim 1, being non-removably attached to the base of a pressurised canister for a metered dose inhaler.

* * * * *